United States Patent [19]

Horstmann et al.

[11] Patent Number: 5,629,003
[45] Date of Patent: May 13, 1997

[54] RAPIDLY DISINTEGRATING SHEET-LIKE PRESENTATIONS OF MULTIPLE DOSAGE UNITS

[75] Inventors: Michael Horstmann, Neuwied; Wolfgang Laux, Dietz; Stefan Hungerbach, Nörtershausen, all of Germany

[73] Assignee: LTS Lohmann Therapie-Systeme GmbH & Co. KG, Neuwied, Germany

[21] Appl. No.: 300,115

[22] Filed: Sep. 2, 1994

Related U.S. Application Data

[63] Continuation of Ser. No. 988,372, Dec. 4, 1992, abandoned, which is a continuation of Ser. No. 709,941, Jun. 4, 1991, abandoned.

[30] Foreign Application Priority Data

Jun. 7, 1990 [DE] Germany ............................ 40 18 247.9

[51] Int. Cl.$^6$ ............................ A61K 7/00; A61K 9/42; A61K 9/70
[52] U.S. Cl. ............................ 424/401; 424/439; 424/447; 424/476; 424/478; 424/479; 424/480; 424/488; 424/49
[58] Field of Search ............................ 424/401, 441, 424/443, 465, 485, 488, 48; 206/363, 368–370, 531, 534.1, 823, 828

[56] References Cited

U.S. PATENT DOCUMENTS

| | | | |
|---|---|---|---|
| 352,466 | 11/1886 | Huttemeyer | 424/440 |
| 2,852,433 | 9/1958 | Hiatt | 167/82 |
| 4,128,445 | 12/1978 | Sturzenegger et al. | 156/64 |
| 4,136,145 | 1/1979 | Fuchs | 264/164 |
| 4,683,256 | 7/1987 | Porter et al. | 424/439 |
| 4,777,046 | 10/1988 | Iwakura et al. | 424/435 |
| 4,906,488 | 3/1990 | Pera | 426/573 |
| 5,077,053 | 12/1991 | Kuncewitch et al. | 424/441 |

FOREIGN PATENT DOCUMENTS

| | | | |
|---|---|---|---|
| 2028224 | 12/1970 | Germany | 424/472 |
| 2009597 | 6/1978 | United Kingdom . | |

*Primary Examiner*—Neil S. Levy
*Attorney, Agent, or Firm*—Sprung Horn Kramer & Woods

[57] ABSTRACT

A presentation which, in the form of a film, permits the individual dosage of drugs, confectionary, other food, cosmetics and the like for oral application or intake. The presentation is characterized by the fact that it comprises a mass of 20 to 60%-wt. of at least a film former, 2 to 40%-wt. of at least a gel former, 0.1 to 35%-wt. of at least an active substance, and up to 40%-wt. of an inert filling agent, being applied on a carrier, or by consisting of a mass having the aforementioned composition but is unsupported. In the production thereof, an intimate mixture of said components is prepared, optionally with the addition of up to 30%-wt. of a polar solvent, and processed to form a homogeneous, spreadable or extrudable mass.

7 Claims, No Drawings

RAPIDLY DISINTEGRATING SHEET-LIKE PRESENTATIONS OF MULTIPLE DOSAGE UNITS

This application is a continuation of application Ser. No. 07/988,372, filed Dec. 4, 1992, now abandoned, which is a continuation of application Ser. No. 07/709,941 filed Jun. 4, 1991 now abandoned.

DESCRIPTION

The present invention relates to sheet-like forms of administration of drugs, confectionary, other food, cosmetics and the like for oral application or intake.

Presentations of drugs, sweets and other foodstuffs, as well as cosmetics which are to be applied in the oral region or have to be taken by deglutition, in principle, can either be freely dosed by the applicant or are already pre-divided into dosage units by the manufacturer. Such prepared forms are particularly common in pharmaceutics in the form of tablets, capsules, coated tablets, pills, vials and the like. Compared to dropping-solutions, ointments, or creams which have to be dosed by the user, unintentional wrong dosage by applicant is avoided in these cases.

From the application technological point of view, tablets must have a certain minimum size (5 to 6 mm diameter) and a certain minimum weight (approximately 100 to 200 mg), in order to ease handling of these presentations. Thus, highly efficacious drugs may contain about 99% of inactive ingredients, relative to the tablet weight.

Even foodstuff, in particular confectionary, is frequently found on the market in individually dosed form (candies, sweetener tablets, peppermint lozenges, etc.). In this case too—for instance as regards candies—there is the wish to achieve the desired sensation of taste using less "adjuvants" (here usually sugar).

For this reason many technical proposals have been made recently; they are aiming at a reduction of the amount of inactive ingredients in presentations and, at the same time, ensuring safe handling of these substances.

A proposal of particular interest in this connection is the production of sheet-like active substance carriers, e.g., as disclosed by DE 35 34 983, DE 27 46 414, BE 637 363, DE 24 32 925, or DE 36 30 603.

According to the known production processes such paper like carriers are manufactured without any active substance first, and they are then sprayed (e.g. GB 1 061 557) with an active substance-containing solution or coated/printed with an active substance-containing layer of higher concentration (e.g. EP 0 219 762).

However, common complete or partial dissolution of active and inactive substances in water or other solvents (DE 24 49 865) followed by spreading—or casting (e.g. JP 69026674)—and drying may be expected to be the process of choice for the skilled artisan. Extrusion under the action of heat was also proposed (Research Disclosure, 1986, No. 263, March, 145 to 146 (No. 26341).

Film-like presentations offer a great variety of possibilities to separate the individual doses. They can be imagined to have the form of sheets of stamps in which the portion is taken out of the complete composite only a short time prior to use (e.g. BE 637 363, EP 0 219 762). Individual doses of different size can be offered on a tape-like presentation as well, e.g., separated by perforation (e.g. DE 27 46 414). In particular when an inedible carrier is used (e.g. DE 36 30 603), complete separation into individual portions is indicative; this permits a more hygienic, comfortable, and safe removal.

Although a number of flat-shaped forms of administration and processes for the production thereof are known in the art, there still is a considerable lack as to the galenic composition, i.e., the selection of adjuvants, and as to the conception of the physico-chemical fine structure of such sheet-like carriers. Many purposes and aims have to be taken into consideration: Rapid disintegration is required for many drugs to allow rapid swallowing of the dosage unit; other circumstances, in turn, require that the drug temporarily sticks on the mucous membrane of the mouth, and in other occasions—e.g., in case of a medicinal agent with short-time action—a considerably retarded disintegration is desired. In case of sweets, a medium retention time in the mouth, e.g., of flavoring substances, will in general be desirable. Cosmetic, film-like toothpastes should be flexible and disintegrate as soon as possible. In general, sheet-like presentations may not be too fragile so as to ensure safe transfer of the portions to the place of destination. If a carrier is used, both materials must have an adhesion behavior exactly adapted to each other; this is for two reasons: on the one hand, the separation of the doses, e.g., by means of partial punching and peeling off the partitioning inserts, is ensured during production, and, on the other hand, the bond to the carrier is effected even during storage. If drying is required during the production, it should be possible to render the formulation spreadable with the least possible solvent proportion (preferably water) so that the energy involved during drying may be maintained as low as possible.

The galenic compositions known until today, do not satisfy these requirements. Basic principles of the tablet technology are described in connection with film-like tapes by DE 27 46 414; that is the use of optionally thermoplastic binders and other auxiliary agents, the chemical cross-linking, or the addition of hydrophobic substances to delay the disintegration, the combination of several layers and the use of micro-encapsulated active substances. Conventional tablet-disintegrants are used therein as disintegration auxiliaries for films. According to our own findings, the proposals cannot cope with the new pharmaceutic products. The classic disintegrants require a porous, mechanically stable surrounding created by bonding forces between the particles, if they are to cause disintegration through swelling by water addition, or by stored Hooke's deformation energy. However, these preconditions do not exist in case of sheet-like presentations which always remain slightly flexible and are of low porosity. Swelling particles may even delay the disintegration of the films due to withdrawal of water.

According to DE 24 32 925 a formulation contains water-soluble cellulose ethers and separating agents and, optionally, fillers. Since, however, a predominating portion of water-soluble polymers always requires the addition of a large amount of water to achieve a sufficiently low viscosity of the mass being ready to spread or cast, this structure involves high drying cost during fabrication.

In addition, the adhesive bond to the base is affected due to such an extreme material shrinkage. When sheet-like forms of applications are produced by spreading water-base masses to a paper or film which were rendered dehesive, the liquid readily drops-off the support or at least forms zones of different film thicknesses due to the surface tension. Although the viscosity may be increased by adding cellulose derivatives, etc., spreading through the small gap will become more difficult. According to other sources (e.g., DE 35 34 981, DE 36 30 603) viscosity formers are therefore preferred; they result in low-viscosity solutions in the heat (in the coating machine), immediately afterwards, however, provide gel-like, stabilized films on cooling, which then perfectly dry in the air, e.g., agar-agar or gelatin. However, this method cannot satisfy because drying does not permit the application of high temperatures since the mass drops-off again. The drying of such wet masses at low temperatures is uneconomic due to the long dwell times in the apparatus.

It was accordingly the object of the present invention to provide a sheet-like, individually dosed presentation which rapidly disintegrates in water. It was a further object of the present invention to provide a process for the production of such presentations. This process requires only a very small amount of water for processing to achieve sufficient fluidity for dosage by means of knife or roll coating procedures but nevertheless provides a film of uniform thickness on a dehesive carrier; in dry condition good adherence to the carrier is achieved, at the same time, however, easy removal from the carrier, both during subsequent treatment, e.g., during separating by punching, and prior to application is possible.

This object is achieved according to the present invention by a presentation which in the form of a sheet permits single dosage of drugs, confectionary and other food, cosmetics, and the like intended for oral application or intake, and which is characterized by the fact that it comprises a mass consisting of 20 to 60%-wt. of at least one film-forming agent, 2 to 40%-wt. of at least one gel-forming agent, 0.1 to 35%-wt. of at least one active substance, and up to 40%-wt. of at least one inert filling agent being applied on a carrier, or which is unsupported and consists of a mass having the aforementioned composition. The object to provide a process for the production of such a form of administration was achieved by preparing an intimate mixture of the above mentioned components, optionally with adding up to 30%-wt. of a polar solvent, and processing it to a homogeneous, spreadable or extrudable mass. In this connection, the indications of the percentage by weight relate to the solvent-free mass of the four basic components.

Surprisingly, the formulations according to the present invention may be rendered spFeadable by adding only a small amount of a polar solvent. In contrast to the formulations known in the art, they result in uniform films on adehesive carriers already in cold condition. In dried condition, the products may be separated by punching them in such a way that the individual doses may remain on a common carrier already used for spreading and drying. The presentation according to the present invention completely disintegrates in the mouth within 10 minutes, and may exclusively be manufactured of components admissible under the present German Law on Food Products.

Suitable fillers include carbonates, phosphates, silicates, sulfates, and oxides of the alkaline earth metals, zinc oxide, silicas, cellulose and the derivatives thereof, talc or titanium dioxide; however, slightly soluble sugars or derivatives thereof, such as lactose, or starch derivatives, such as cyclodextrins may be used as well, provided that they are present in the products in a substantially undissolved form so that they meet the mechanical properties of a filler.

The term film formers is to embrace ingredients, such as sugars, sugar alcohols and the derivatives thereof, e.g., cane sugar, sorbitol, mannitol, xylitol, glucose, fructose, lactose, galactose, low-molecular organic acids, such as succinic acid, malic acid, or adipic acid, polyethylene glycol, or mixtures of these substances, for example, honey.

The third essential component according to the present invention is a gel former being swellable in water and which, in general, is composed on the basis of polymeric carbohydrates, e.g., starch and the derivatives thereof, agar-agar, alginic acid, arabinogalactans, galactomannan, cellulose and the derivatives thereof, carrageen, dextran, tragacanth, and many gums of vegetable origin. However, synthetic polymers soluble or swellabe in water may also be used according to the present invention, examples thereof include polyvinyl-pyrrolidone, polyvinyl alcohol, polyacrylic acid, or polyacrylamide. Even polypeptides, such as gelatin, albumin, collagen, or eggwhite may be used.

A component acting as filler, the film former and the gel former are essential components giving the product the desired properties but only on the condition that when the quantity of formulation is determined they are processed commonly and in accordance with the individual substance properties. In this connection, a filler or an active agent acting as filler may be used. The above mentiond advantageous properties result, if certain intervals of mixture ratios are maintained: Of film former 20 to 60%-wt., of gel former 2 to 40%-wt, of active substance 0.1 to 35%-wt., and of filler up to 40%-wt.

The layer thickness of the mass amounts to 0.003 to 4 mm, preferably 20 to 400 µm, and in particular 70 to 150 µm.

Processing may be conducted according to processes known to the skilled artisan. In general, the starting components will be premixed in dry condition, and then they will be transformed to a spreadable consistency under stirring by adding a polar solvent in an amount not exceeding 30%-wt. The use of homogenizers to render the mixture more intimate, or the application of a vacuum to remove air bubbles may be useful.

Dispersing and grinding devices having floating grinding elements (ball mills) are preferred in this connection. The application of heat may accelerate the dispersion process and provide the desired physicochemical property of the initial products, however, this depends on the special properties of the gel and film formers.

The addition of water may possibly be unnecessary, if the film-forming agent melts. A superficially homogeneous spreadable or extrudable mass results. Shaping in general is carried out by means of spreading/knife coating or extrusion processes in which the mass passes a gap of defined diameter, e.g., a slot die of an extruder, thus giving it the outer shape. If a solvent is still present, this is at least partially withdrawn in suitable drying devices known to the skilled artisan.

The product is advantageously dried on a carrier to which it sticks due to adhesion even after drying. If, due to process technology, it is not possible to achieve a sufficient thickness of the initial product, two or more layers may be laminated on top of each other by pressure and, if necessary, heat.

Division into the individual doses is effected by cutting, punching, embossing or similar processes providing areas of defined size which are separated or separable. If drying is effected on a carrier, the presentation may remain on this carrier after said separation procedure until it is applied; this considerably eases taking it off.

The present invention will be illustrated in more detail by the following examples:

EXAMPLE 1

75 g acetylated starch
62 g honey
55 g calcium sulfate dihydrate
5 g citric acid
50 g water are mixed in a closed stirring apparatus and heated to 50° C. The mixture is homogenized under stirring for two hours and subsequently cooled to room temperature. Stirring is continued for half an hour under vacuum and the evaporated water is added again.

2 ml of peppermint oil are added and incorporated by stirring over a 5-minute period.

The homogeneous mass is spread on siliconized paper with a coating device at a gap width of 500 μm and dried at 80° C. for 15 minutes.

Cuts outlining the later shape are inserted into the dried mass without damaging the paper carrier by means of suitable cutting devices. The material remaining between the obtained individually dosed presentations is removed in one process step by mechanical withdrawal. To protect the presentations from drying-up, groups of each 12 of them being placed on a common piece of paper carrier are sealed into a composite packaging material of paper/aluminum/ethylenevinyl-acetate which is substantially impermeable to water vapor.

Use: flavor carrier (sweets)

EXAMPLE 2

100 g polyethylene glycol (molecular weight approximately 1,500 g/mol)
8 g carboxyvinyl copolymer
are kneaded until homogeneous in a heatable double-Z-kneader at 80° C. (duration: 2 hours)
70 g lactose
are added and kneaded into the basic mass within 30 minutes. The temperature is reduced to 50° C.
8 g glibenclamide
are added; the preparation is kneaded for another 30-minute period. The hot mixture is filled into a plunger-type extruder (available volume: approximately 150 ml) which has been pre-heated to 50° C. Extrusion is started immediately and at a conveyance speed of approximately 10 g/min through a 10×1 mm sheet die; cooling until solidified on a cold, clean working surface. The resulting extrudate is divided into sections of 10 mm by means of a knife. An orally administrable form of a drug with approximately 3 mg of active substance and a weight of approximately 80 mg results which disintegrates in the mouth.

EXAMPLE 3

25 g acetylated starch
20 g sorbitol
30 g calcium carbonate
1 g titanium dioxide
22 g water
8 g glycerol
are mixed in a closed stirring apparatus and heated to 50° C. The mixture is homogenized under stirring within two hours and subsequently cooled to room temperature.

Stirring is continued for half an hour under vacuum, the evaporated water is compensated. 0.5 ml of peppermint oil is added and homogeneously incorporated by stirring over a 5-minute period. The mass is spread on siliconized paper with a coating device at a gap width of 500 μm and dried at 80° C. for 10 minutes.

Cuts outlining the later shape are inserted into the dried mass without damaging the paper carrier by means of a suitable cutting device. The material remaining between the obtained individually dosed presentations is removed by mechanical peeling. On the paper carrier each presentation is individually sealed into a paper/aluminum/ethylenevinylacetate-composite packaging material which is substantially impermeable to water vapor.

Use: instant toothpaste

EXAMPLE 4

600 g acetylated starch
440 g calcium sulfate dihydrate
40 g citric acid
are weighed into a porcelain ball mill provided with 10 grinding elements (diameter appr. 4 cm) and premixed in dry condition in the closed mill at 10 rpm for 1 hour. A suspension of
20 g titanium dioxide in
550 g water
is added and the mixture agitated under the same conditions for one hour.

500 g of honey are added. Homogenization is continued at 10 rpm for 2 hours. Finally, 16 ml of peppermint oil are added and rotation continued for 18 hours. The further treatment of the mass thus obtained is effected as described for Example 1.

It is understood that the specification and examples are illustrative but not limitative of the present invention and that other embodiments within the spirit and scope of the invention will suggest themselves to those skilled in the art.

We claim:

1. A sheet comprising multiple dosage units which disintegrate in water and which contain as active substance, a cosmetic, perfrming or flavoring application, and comprising a mass of (a) 20–60%-wt. of at least one film-forming agent,
   (b) 2–40%-wt. of at least one gel-forming agent,
   (c) 0.1–35%-wt. of at least one active substance and
   (d) up to 40%-wt. of at least one inert filling agent, the percentage relating to the solvent-free mass of these four components and the dosage units being supported on a carrier, wherein the film former comprises a compound selected from the group consisting of monomeric and oligomeric sugars, sugar alcohols, organic acids having up to 6 carbon atoms and polyethylene glycol, wherein the gel former is water swellable and consists of at least one component selected from the group consisting of polymeric carbohydrates, esters thereof, gelatin, albumin, collagen, egg white, carboxyvinyl copolymers, polyacryl amide, polyvinyl pyrrolidone and polyvinyl alcohol, wherein the filler comprises at least one physiologically acceptable compound selected from the group consisting of carbonates, phosphates, silicates, sulfates and oxides of an alkaline earth metal, silicas, slightly soluble sugars, cellulose, cyclodextrin as a starch derivative, talc, titanium dioxide, zinc oxide and magnesium stearate, undissolved or crystalline partial amounts of active substances simultaneously acting as filling agents, and wherein the layer thickness of the dosage units is from 0.003 to 4 mm.

2. A sheet presentation according to claim 1, comprising at least two active substance-containing layers.

3. A sheet according to claim 1, wherein the layer thickness of the dosage units is from 20 to 400 μm.

4. A sheet according to claim 3, wherein the layer thickness is from 70 to 150 μm.

5. A sheet according to claim 1, wherein the active substance is of organic nature.

6. A sheet according to claim 1, which is provided with a release paper or a release film and is divisible into individual doses of areas of defined size.

7. A sheet according to claim 1, wherein the multiple dosage units comprise an instant toothpaste composition.

* * * * *